US006777199B2

(12) United States Patent
Bull et al.

(10) Patent No.: US 6,777,199 B2
(45) Date of Patent: *Aug. 17, 2004

(54) RAPID QUANTITATIVE MEASUREMENT OF SOLUBLE FIBRIN IN OPAQUE BODY FLUIDS

(75) Inventors: Brian S. Bull, Loma Linda, CA (US); Ralph A. Korpman, Nashville, TN (US); Karen L. Hay, Redlands, CA (US)

(73) Assignee: Medical Devices Corporation, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/136,037

(22) Filed: Apr. 29, 2002

(65) Prior Publication Data

US 2003/0059836 A1 Mar. 27, 2003

Related U.S. Application Data

(63) Continuation of application No. 09/388,796, filed on Sep. 2, 1999, now Pat. No. 6,436,655, which is a continuation-in-part of application No. 09/021,062, filed on Feb. 9, 1998, now abandoned.

(51) Int. Cl.[7] .................. C12Q 1/56; C07K 14/745; B03D 3/02

(52) U.S. Cl. .............. 435/13; 530/381; 422/73
(58) Field of Search .............. 435/13; 530/358, 530/381; 422/73

(56) References Cited

U.S. PATENT DOCUMENTS 6,436,655 B1 * 8/2002 Bull et al. ............... 435/13

* cited by examiner

Primary Examiner—Marjorie Moran
(74) Attorney, Agent, or Firm—Dorsey & Whitney LLP

(57) ABSTRACT

A method for determining the existence and the amount of soluble fibrin contained in a specimen fluid is provided. The method includes the steps of precipitating soluble fibrin out of the opaque specimen fluid, aggregating the soluble fibrin precipitates in a limited region of a transparent container so as to render the precipitates optically detectable in the opaque specimen fluid, and optically detecting the precipitates. The amount of soluble fibrin may be determined by measuring the time from the addition of the precipitating regent to the detection of the soluble fibrin precipitates. Methods of the present invention allow one to measure soluble fibrin in whole blood, and therefore render the test useful in the operating room under conditions of major surgery and in the presence of severe trauma wherein DIC is likely to supervene.

15 Claims, 3 Drawing Sheets

RAPID QUANTITATIVE MEASUREMENT OF SOLUBLE FIBRIN IN OPAQUE BODY FLUIDS

CROSS REFERENCE TO RELATED ART

A commonly owned and issued U.S. Pat. No. 5,716,796, entitled "Optical Blood Hemostatic Analysis Apparatus and Method" by Brian S. Bull and Ralph A. Korpman, filed on Jan. 29, 1996, is hereby incorporated in its entirety by reference.

This application is a continuation of Ser. No. 09/388,796 filed Sep. 2, 1999 now U.S. Pat. No. 6,436,655, is a continuation-in-part of the application Ser. No. 09/021,062, entitled "A Rapid Quantitative Measurement of Soluble Fibrin In Whole Blood," filed on Feb. 9, 1998, now abandoned, the content of which is incorporated herein by reference.

BACKGROUND OF THE INVENTION

Area of the Art

The invention relates generally to optical blood hemostatic analysis methods and specifically to methods for quantitatively measuring the concentration of soluble fibrin molecules in opaque body fluids such as whole blood.

DESCRIPTION OF THE PRIOR ART

Soluble fibrin (SF) molecules are generated from fibrinogen molecules when thrombin cleaves the alpha and beta polypeptide chains of the fibrinogen molecules. The presence of SF molecules in the blood stream is one of the most sensitive indicators of early disseminated intravascular clotting (DIC). DIC poses a great threat to patients during major surgery and after severe trauma. Therefore, a technique for rapidly and quantitatively measuring levels of soluble fibrin in whole blood would be very useful during major surgery and after severe trauma.

Although the measurement of SF has been carried out for many years, the measurement of soluble fibrin under the circumstances of major surgery or severe trauma has always been problematic and the technique is seldomly used. All available techniques for SF measurement require that the procedure be run on plasma rather than on whole blood; such a procedure takes additional time. In addition, most available techniques are only semiquantitative (the results are in the form of (+−++++)). These problems have prevented the test from being widely used. Available techniques must utilize plasma because the detection of SF precipitates is done optically and a clear fluid medium is thus a necessity. In addition, in those techniques, optical endpoints are desirable for tests of the coagulation process as they typically permit the entire reaction chamber to be disposable. Optical endpoints for SF in whole blood are typically useless, however, owing to the opacity of the whole blood and the widely distributed nature of the SF precipitates. Therefore, the previous techniques that utilize optical endpoints require the use of plasma.

Plasma is prepared from whole blood by centrifugation. The centrifugation step typically requires the sample to be transported out of the operating room to an analytical laboratory. The minimum time for a test result thus becomes 30–45 minutes. Once the transport time has been added to the time required for centrifugation and the time for analysis, the test result is useless in the context of the operating room as the patient's condition would have likely changed substantially in the meantime. For studying the kinetics of SF conducting a test that requires preparation of plasma is likewise problematic as the reaction of thrombin on fibrinogen takes place on the order of seconds and cannot be stopped without using anti-polymerizing agents that interfere with subsequent detection of SF.

Most available methods for detection of SF quantify the amount of SF present only in a very approximate manner as in +−++++. Those that do a more rigorous quantification require additional steps such as:

1. removing the SF precipitates, drying and weighing the precipitates;
2. removing the SF precipitates, analyzing them for protein content;
3. Immunologically precipitating the SF precipitates, using a second antibody to quantify the amount.

All of these techniques add even more time to the SF analysis. They render the test less useful as a result.

Therefore, a need exists to develop a method that performs a SF test in an opaque suspension such as whole blood. Such a method would have far greater utility than presently available tests which, due to their optical endpoints, must be performed in plasma. Indeed, it is only whole blood tests that can be utilized in an operating room where the rapid measurement of SF will permit the surgeon or the anesthesiologist to take immediate steps to correct the conditions that are leading towards DIC.

SUMMARY OF THE INVENTION

It is an object of the present invention to provide a method for rapidly quantifying soluble fibrin optically in opaque suspensions of whole blood so as to render the test useful in the operating room under conditions of major surgery and in the presence of severe trauma where DIC is likely to supervene.

These objectives and advantages are achieved by a method of the present invention. In accordance with the embodiments of the present invention, the method includes the steps of:

(a) mixing a portion of the opaque specimen fluid in a transparent container with a sufficient amount of precipitating reagent under a condition that causes the soluble fibrin to precipitate;

(b) aggregating and concentrating the soluble fibrin precipitates in a region of the container for rendering the precipitates optically detectable in the opaque specimen fluid;

(c) optically detecting the precipitates;

(d) recording the time when the precipitates are first become optically detectable in the opaque specimen fluid, wherein the time elapsed from the addition of the precipitating reagent to the detection of the aggregated precipitates is an inverse measure of the quantity of soluble fibrin present in the opaque specimen fluid.

A method in accordance with the present invention provides a number of advantages. As explained in greater detail below, the methods of the present invention provide a rapid and quantitative measurement of soluble fibrin in opaque body fluids such as, but not limited to, whole blood. Particularly, methods of the present invention make it possible to use optical endpoints to measure SF in whole blood. It is known in the art that optical endpoints are desirable for tests of the coagulation process as they typically permit the entire reaction chamber to be disposable. However, prior to the present invention, optical endpoints for SF in whole blood are typically useless owing to the opacity of the whole blood and the widely distributed nature of the SF precipitates. The present invention allows SF to form precipitates and to be collected in a small, predictable portion of the reaction mixture so that they can be readily detected optically. When collected in high concentration, SF precipitates exclude the opaque whole blood medium and become optically detectable from outside the reaction chamber. Methods of the present invention eliminate the plasma preparation steps, and provide rapid and effective SF measurements that are readily usable in the operating room under conditions of major surgery and in the presence of severe trauma where DIC is likely to supervene. Since the present invention can accurately detect and measure the amount of soluble fibrin in an opaque specimen fluid, the present invention provides an effective means to detect early disseminated intravascular clotting.

The methods of the present invention are well suited for use during major surgery, after severe trauma, and similar circumstances where disseminated intravascular clotting poses its greatest threat. A method in accordance with the present invention can effectively detect DIC by rapidly and quantitatively measuring the soluble fibrin.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which:

FIG. 1c is a diagrammatic view of the apparatus shown in FIG. 1a.

DETAILED DESCRIPTION OF THE INVENTION

Figure 1A:
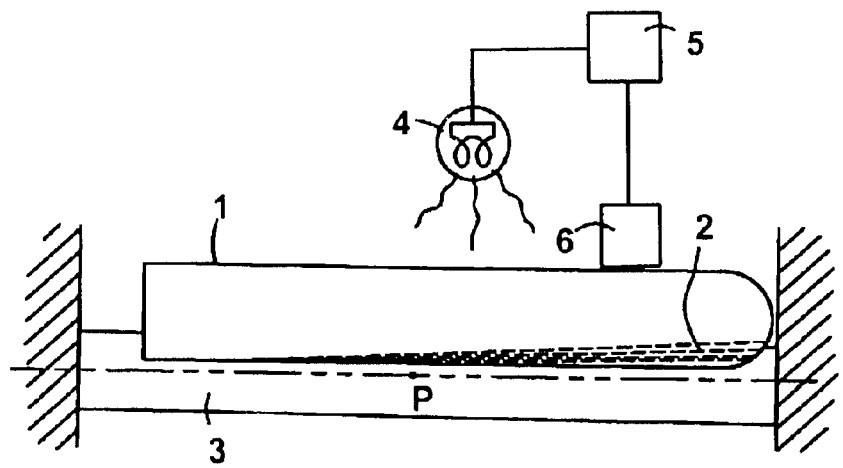
FIGS. 1a and 1b are diagrammatic side views of one embodiment of the invention, showing the two positions in the rocking motion of the apparatus.

One aspect of the present invention provides a method for determining the existence and the amount of soluble fibrin contained in an opaque specimen fluid. In accordance with embodiments of the present invention, the method comprises the steps of:

(a) mixing a portion of the opaque specimen fluid in a transparent container with a sufficient amount of precipitating reagent under a condition that causes the soluble fibrin to precipitate;

(b) aggregating and concentrating the soluble fibrin precipitates in a region of the container for rendering the precipitates optically detectable in the opaque specimen fluid;

(c) optically detecting the precipitates;

(d) recording the time when the precipitates are first become optically detectable in the opaque specimen fluid, wherein the time elapsed from the addition of the precipitating reagent to the detection of the aggregated precipitates is an inverse measure of the quantity of soluble fibrin present in the opaque specimen fluid.

For purposes of the present invention, the opaque specimen fluid can be any body fluids that contain soluble fibrin. The inventions are, however, particularly applicable to opaque body fluids such as whole blood, bloody effusions, bloody cerebrospinal fluid and the like. Preferably the specimen fluid is whole blood. In one embodiment of the present invention, whole blood is diluted. The whole blood can be diluted by a diluent such as saline solution.

A precipitating reagent is any reagent which can cause soluble fibrin to precipitate out of the soluble fibrin-containing specimen fluid. Examples of a precipitating reagent include, but are not limited to, protamine sulfate, polybrene, and the like. Preferably, the precipitate reagent is protamine sulfate.

The amount of a precipitating reagent is sufficient if it can cause substantially all of the soluble fibrin contained in a specimen fluid to precipitate out of the fluid. One skilled in the art can readily determine the amount of the precipitating reagent that should be used without undue experimentation in view of the instant disclosure.

A portion of the opaque specimen fluid is mixed with a precipitating reagent under a condition that causes the soluble fibrin to precipitate. In one embodiment of the present invention, the mixing may take place at a pH of about 5.9 or below, and at a temperature of about 37° C.

According to embodiments of the present invention, the soluble fibrin precipitates contained in a transparent container may be aggregated and concentrated to a limited region of the container by placing the transparent container to an apparatus of the present invention. The apparatus used in the present invention must have the characteristics of producing in the reaction mixture hydraulic flow patterns so that the apparatus will aggregate and concentrate the SF precipitates in a highly localized portion of the reaction mixture so as to render them visible in an opaque medium such as diluted whole blood. In one embodiment of the present invention, an optical blood homeostatic analysis apparatus as described in U.S. Pat. No. 5,184,188, the relevant content of which is incorporated herein in its entirety by reference.

In general, an optical blood hemostatic analysis apparatus is capable of both rotating and rocking a transparent, approximately cylindrical specimen container (for example, a 12×75 mm glass test tube) while maintaining the container in a nearly horizontal position and at a temperature of approximately 37° C. Specimen fluid and a precipitate reagent are introduced into the open end of the container, and are then mixed and incubated by the apparatus.

Figure 1B:
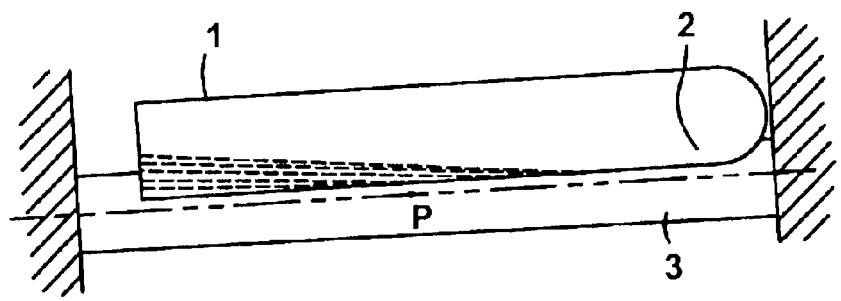
Figure 1C:
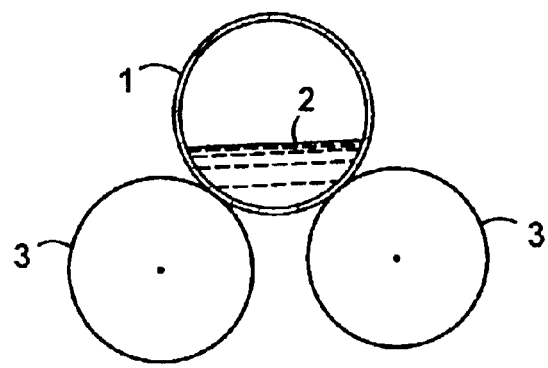

As described in the '188 patent, one embodiment of the mechanical apparatus of the invention is illustrated in FIGS. 1a and 1b, which show a specimen container 1 containing specimen fluid 2, which is supported in a nearly horizontal position on a pair of rotating rollers 3. FIG. 1c is an end-view of the apparatus shown in FIGS. 1a and 1b. The rollers 3 may be rotated by any convenient means, such as an electrical motor coupled to the rollers either directly or through a drive train (e.g., a belt, gears, or a friction drive). In the preferred embodiment, the specimen container 1 is rocked longitudinally around an approximate mid-point pivot P through an angle of preferably about ±3°, as shown by comparing FIG. 1a with FIG. 1b. The rotational rate of the specimen container 1 is typically about 12 rpm, and the rocking rate is typically about 15 cycles per minute. The rocking motion may be imparted by a cam or any other convenient means. The specific rocking and rotation rates are not necessarily critical, but the particular values described above have been found to be effective.

The specimen fluid 2 does not run out of the open end of a small-diameter specimen container 1 when tilted forward because of the strong surface tension of the contained fluid, aided by the small radius of curvature of the rim of the container 1. During the rotating and rocking, the precipitating reagent causes the soluble fibrin contained in the diluted whole blood to precipitate out of solution. As the precipitation reaction is occurring, the rocking and rotating motion moves the not-yet-visible fibrin monomer (SF) clumps to a region where all of the SF in the entire sample will accumulate. As they reach this preferred region the clumps interact with SF material already there making the location even more attractive for SF accumulations that are still too small to be detected optically. If the amount of SF is sufficiently large, the SF precipitates will adhere to the inner tube surface and be lifted clear of the reaction mixture.

The time the precipitates first become optically detectable is defined as the first end-point. The time the precipitates stick to the tube and rotate with the tube is defined as the second end-point. The time that it takes from the start of the process to the first end-point, and to the second-end point will be measured. The time measurements can be correlated to the quantity of SF by a standard curve respectively. The SF standard curve is produced by adding known quantities of SF to native whole blood and analyzing the resulting mixtures.

For the purpose of determining the quantity of SF in a specimen fluid, one may use either of the time measurements or both to determine the quantity of SF with a standard curve. The time that it takes from the start of the process to the second-end point is easier to measure. However, when the level of SF is low, the first end-point may be the only one available since the precipitates may not be concentrated enough to reach the second end-point. In this case, it is preferred to use the time measurement of the first end-point to determine the quantity of SF. Any comparable means of accomplishing this goal is within the scope of this invention, including simple rotation or agitation of a sealed container, or use of a container having a liquid retention rim at its opening.

Since the process works best at 37° C., it is desirable to maintain the specimen at that temperature. The temperature of the specimen fluid can be maintained, for example, by a tungsten filament light bulb 4 situated near the specimen container 1 and controlled by a thermostatic circuit 5 having a temperature sensor 6 adjacent to or in contact with the specimen container 1. Alternatively, the temperatures can be maintained by placing the specimen container 1 in an incubated chamber having the desired temperature.

The time that it takes from the start of the process to the end-points can be measured by a variety of means that detect the end-points. A number of different types of end-point detectors can be used in the invention. Examples of types of end-point detectors include, but are not limited to, direct visual observation; a flying spot scanner; a charge couple device (CCD) camera, a detector consisting of a narrow beam of light (e.g., from a small, solid state laser) that is caused to sweep (e.g., by means of an oscillating mirror) the inner wall of the transparent specimen container from a position just outside the open end of the container; and a detector that uses a light beam and a time-delay discriminator circuit which distinguishes the presence of soluble fibrin precipitates from the rocking surface of the blood itself. The above detectors are fully described in the '188 patent, the content of which is incorporated herein by reference.

It is to be understood that the optical blood hemostatic analysis apparatus described above has been chosen only for the purpose of describing a particular embodiment and function of the invention. Other types of optical apparatus may also be used as long as the apparatus can perform the same function as the one described above. Suitable apparatus would be evident to those of ordinary skill in the art in view of this disclosure.

In one embodiment of the present invention, the measurement steps are repeated with a second precipitating reagent. In accordance with this embodiment, the measurement method further includes the steps of mixing another portion of the opaque specimen fluid with a second precipitating reagent and repeating steps (a) to (d) described above to obtain a second timing measurement for elapsed time. Then the first timing measurement and the second timing measurement are related to respective standard curves prepared with respective first and second precipitating reagents. The quantity of soluble fibrin present in the opaque specimen sample is determined by an average of the two measurements. For the purpose of the present invention, the first and the second precipitating reagents may be the same reagents at different concentrations or may be two different reagents.

It should be understood that portions of an opaque specimen fluid may be mixed respectively with two or more different concentrations of a precipitating reagent to obtain two or more measurements, and the quantity of SF contained in the specimen fluid may be determined by averaging the measurements. Alternatively, portions of an opaque specimen fluid may be mixed with two or more different types of precipitating reagents to achieve the same results.

EXAMPLE I

The Kinetics of the Production of SF in Whole Blood

A method of determining soluble fibrin with the present invention is used to measure the amount of SF in a whole blood sample treated with thrombin to determine the kinetics of the reaction. 2 ml of whole blood was mixed with 0.01 NIH units of thrombin at time zero and 150 μl aliquots were removed at the times noted. Each aliquot was suspended in about 450 μl of saline solution at pH 5.0 and was placed in a specimen container together with about 20 μl of the precipitating reagent, protamine sulfate. The time of the appearance of precipitates was measured and recorded in SF units. The results is summarized in Table I.

TABLE I

| Time after Thrombin Addition (min) | SF Time (sec) | Soluble Fibrin Units | Visible Fibrin |
|---|---|---|---|
| 0 | 250 | 2.8 | No |
| 1 | 12.5 | 56.0 | No |
| 2 | 10.2 | 68.6 | No |
| 3 | 9.8 | 71.4 | No |
| 4 | 9.9 | 70.7 | No |
| 5 | 11.2 | 62.5 | No |
| 8 | 13.5 | 51.9 | Yes |
| 10 | 14.4 | 48.6 | Yes |
| 19 | 14.7 | 47.6 | Yes |
| 31 | 17.0 | 41.2 | Yes |
| 70 | 19.4 | 36.1 | Yes |
| 112 | 20.2 | 35.0 | Yes |
| 189 | 21.2 | 33.0 | Yes |

Figure 2:
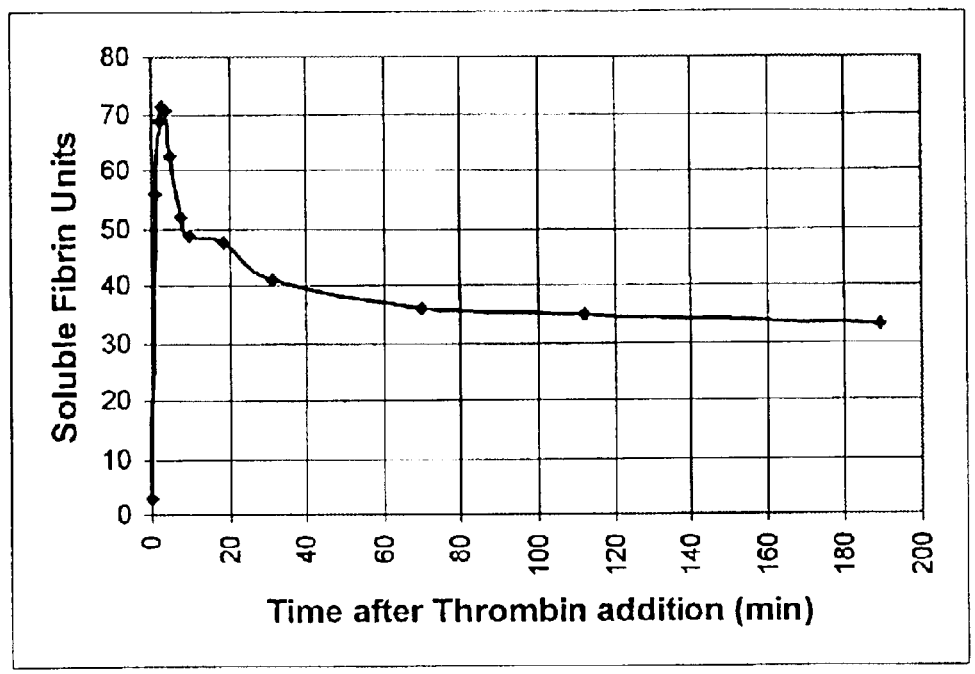
FIG. 2 is a plot of the kinetics of the production of SF in whole blood.

FIG. 2 is a plot of the kinetics of the production of SF in whole blood. At the point marked by the arrow thrombin is added to the reaction mixture. The present invention is utilized to perform analysis at intervals of 1–30 minutes. Over an initial period of 3–4 minutes after the addition of a small quantity of thrombin, the SF concentration titer rises.

The early SF molecules produced can be carried by the fibrinogen and kept from polymerizing as a visible fibrin clot. Following a peak concentration reached at approximately three minutes, the SF present in excess of the carrying capacity of the fibrinogen precipitates out of the mixture in the form of a visible fibrin clot and over the next 30 minutes the level of SF decreases by about 50%. Over the ensuing hours, the SF level declines slightly but is essentially stable for periods in excess of 2 hours.

As noted in FIG. 2, the kinetics of the reaction require a test that can be completed within minutes, hence require that the test be performed in whole blood.

EXAMPLE II

SF Measurement in Whole Blood

In a second test of the system, a series of 150 µl whole blood samples were, at thirty minute intervals, removed from a patient undergoing liver transplantation. These samples were suspended in about 450 µl saline, and were placed in a specimen container together with about 20 µl of the precipitating reagent, protamine sulfate. The whole blood sample was taken from a patient at the start of the operation, then every 30 minutes with samples spaced more closely during the critical reperfusion phase of the transplantation process. The mixture of protamine sulfate and whole blood was placed in a hemostatic analysis apparatus as described in the '188 patent at a temperature of about 37° C. to allow the mixture to react until precipitates formed and adhered to the inner tube surface. The time that it took from the start of the process to the first-end point, and the second end-point were then measured, and the measurements were correlated to the quantity of SF by a standard curve.

Other portions of the same samples were centrifuged to recover plasma and refrigerated until the next day so that additional assays for fibrin degradation products (FDPs), D-dimer levels and fibrinogen levels could be performed. These four assays are plotted in FIGS. 3a and 3b to show the congruence of the results.

Figure 3A:
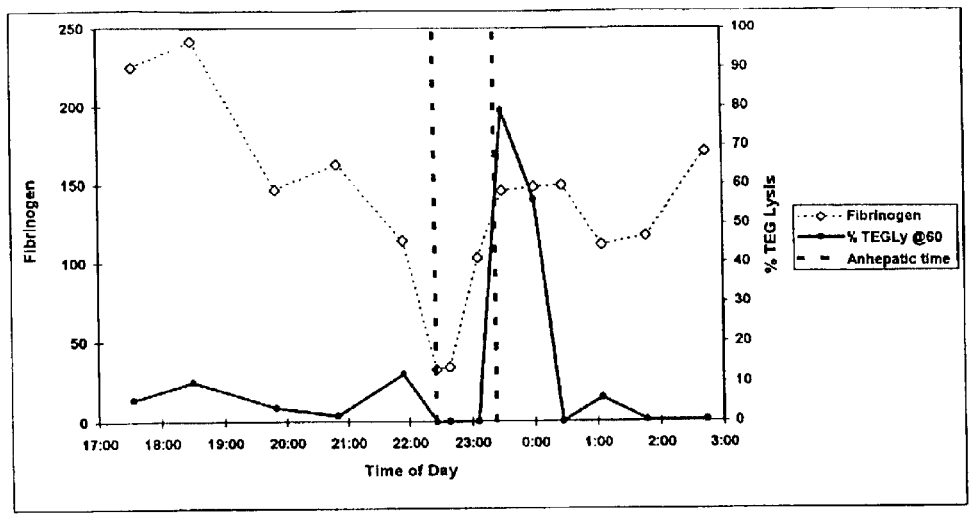
FIG. 3a shows a series of fibrinogen measurements performed on samples from a patient undergoing liver transplantation.
Figure 3B:
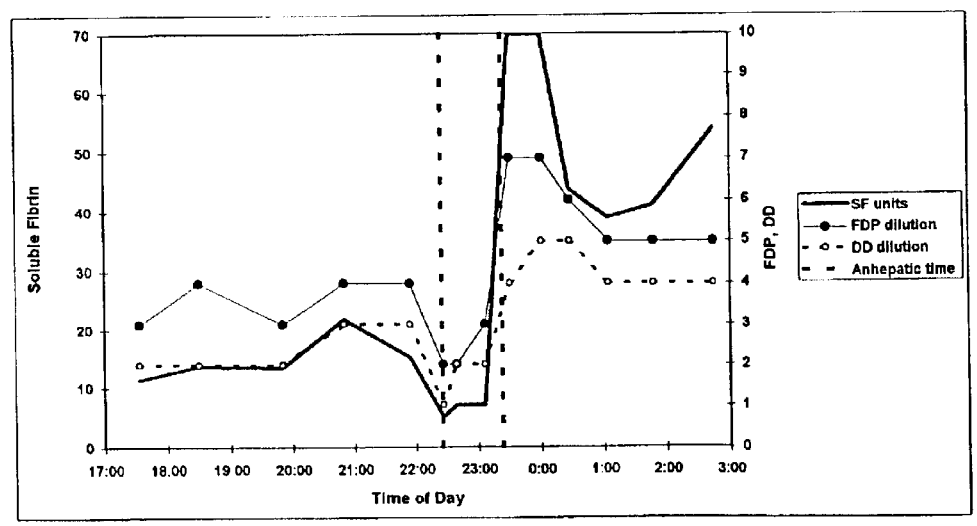
FIG. 3b shows three other assays performed on the same patient: measurements of D-dimer, fibrin degradation products (FDP) and soluble fibrin (SF) in relation to the time of liver replacement.

FIG. 3a is a series of fibrinogen measurements performed on samples from a patient undergoing liver transplantation. FIG. 3b shows three other assays performed on the same patient: measurements of D-dimer, fibrin degradation products (FDPs) and soluble fibrin (SF) in relation to the time of liver replacement. Only the SF tests were performed during the actual surgery. The remaining tests were performed on the following day since all of the remaining tests required the preparation of plasma from the whole blood samples and the patient's condition was changing so rapidly that the values were not useful to the operating surgeon. The close correlation of the various measures on all four test methods indicates that the information provide by the SF assay within minutes of the time the sample was drawn is useful for managing a very unstable patient.

Correlation coefficients are summarized in Table II. Table II confirms the visual impression that all four assays are highly correlated—that as fibrinogen disappears from the patient's circulation SF and the various measures of fibrinogen/fibrin breakdown (FDP, D-dimer) begin to appear.

TABLE II

| Correlation coefficients (r) | |
|---|---|
| 0.9026 | SFU vs FDP dilution |
| 0.8558 | SFU vs D-Dimer dilution |
| −0.8572 | SFU vs Fibrinogen |

The foregoing is meant to illustrate, but not to limit, the scope of the invention. Indeed, those of ordinary skill in the art can readily envision and produce further embodiments, based on the teachings herein, without undue experimentation.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A method for determining the existence and the amount of soluble fibrin contained in an opaque specimen fluid, the method comprising the steps of:
   (a) mixing a portion of the opaque specimen fluid in a transparent container with a sufficient amount of precipitating reagent under a condition to cause the soluble fibrin to precipitate;
   (b) aggregating and concentrating the soluble fibrin precipitates in a region of the container for rendering the precipitates optically detectable in the opaque specimen fluid,
   (c) optically detecting the precipitates,
   (d) recording the time when the precipitates first become optically detectable in the opaque specimen fluid, wherein the time elapsed from the addition of the precipitating reagent to the detection of the aggregated precipitates is an inverse measure of the quantity of soluble fibrin present in the opaque specimen fluid.

2. The method of claim 1 further comprising a step of recording the time when the precipitates stick to the container and rotate with the container, and wherein the time elapsed from the addition of the precipitating reagent to the detection of the sticking and rotating aggregated precipitates is an inverse measure of the quantity of soluble fibrin present in the opaque specimen fluid.

3. The method of claim 1, wherein the step (b) further comprises the step of
   (a) placing the transparent container containing the mixture within an apparatus that is capable of subjecting the container to both rocking and rotating motion; and
   (b) subjecting the mixture contained in the container placed within the apparatus to rocking and rotating motion to aggregate and concentrate the soluble fibrin precipitates in a limited region of the container.

4. The method of claim 1 further comprising a step of relating the recorded time to a standard reference curve measured on samples with a known soluble fibrin content to determine the concentration of soluble fibrin contained in the opaque specimen fluid.

5. The method of claim 1, wherein the precipitating reagent is a first precipitation reagent, and the time recorded in step (d) is a first time measurement, and the method of claim 1 further comprising the steps of mixing another portion of the opaque specimen fluid with a second precipitating reagent and repeating steps (a) to (d) of claim 1 to obtain a second time measurement for elapsed time.

6. The method of claim 5, wherein the first time measurement and the second time measurement are related to respective standard curves prepared with respective precipitating reagents, and the quantity of soluble fibrin present in the opaque specimen sample is determined by an average of the two measurements.

7. The method of claim 5, wherein the first precipitating reagent and the second precipitating reagent are two concentrations of an identical precipitating reagent.

8. The method of claim 5, wherein the first precipitating reagent and the second precipitating reagent are different.

9. The method of claim 1, wherein the opaque specimen fluid is an opaque body fluid from human containing soluble fibrin.

10. The method of claim 1, wherein the opaque specimen is selected from a group consisting of whole blood, bloody effusions, bloody, and cerebrospinal fluid.

11. The method of claim 10, wherein the opaque specimen fluid is a diluted whole blood.

12. The method of claim 1 wherein the precipitating reagent is protamine sulfate or polybrene.

13. The method of claim 1, wherein the portion of the opaque specimen fluid is mixed with the precipitating reagent at a PH of about 5.9 or below and a temperature of about 37° C.

14. The method of claim 7, wherein the precipitating reagents are protamine sulfate or polybrene.

15. The method of claim 8, wherein the first precipitating reagent is protamine sulfate, and the second precipitating reagent is polybrene.

* * * * *